| United States Patent [19] | [11] | 4,125,516 |
|---|---|---|
| Dexter et al. | [45] | Nov. 14, 1978 |

[54] ALKYLTHIOALKANOYLOXYALKYL AND ALKYLTHIOALKYL SUBSTITUTED BIS-HYDANTOIN COMPOUNDS

[75] Inventors: Martin Dexter, Briarcliff Manor; David H. Steinberg, Bronx, both of N.Y.

[73] Assignee: Ciba-Geigy Corporation, Ardsley, N.Y.

[21] Appl. No.: 759,967

[22] Filed: Jan. 17, 1977

Related U.S. Application Data

[63] Continuation of Ser. No. 668,879, Mar. 22, 1976, abandoned.

[51] Int. Cl.$^2$ .................. C07D 233/72; C08K 5/34
[52] U.S. Cl. .................. 260/45.8 N; 544/221; 544/302; 544/314; 548/312; 544/231
[58] Field of Search .................. 548/310; 260/45.8 N
[56] References Cited

U.S. PATENT DOCUMENTS

| 3,852,302 | 12/1974 | Habermeier et al. | 548/310 |
| 3,904,644 | 9/1975 | Jaeger | 548/310 |
| 3,945,982 | 3/1976 | Morgan | 548/312 |

FOREIGN PATENT DOCUMENTS 75-106,881  8/1975  Japan.

OTHER PUBLICATIONS

MacFadyen, Chem. Abst. 1975, vol. 83, No. 132572m.

*Primary Examiner*—Natalie Trousof
*Attorney, Agent, or Firm*—Luther A. R. Hall

[57] ABSTRACT

Alkylthioalkanoyloxyalkyl and alkylthioalkyl derivatives of N-heterocyclic moieties are stabilizers for organic materials subject to oxidative, thermal and/or light induced deterioration. They are prepared by classical transesterification, oxirane ring opening and addition of mercaptan to olefin reactions. Typical embodiments are tris[2-(3-n-dodecythiopropionyloxy)ethyl isocyanurate] and 3-(3-n-dodecylthio-2-hydroxypropyl)-5,5-dimethylhydantoin. These compounds are used in conjunction with phenolic antioxidants to stabilize organic materials, particularly polyolefins and hydrocarbon compositions, against the deleterious effects of heat and oxygen and against discoloration.

8 Claims, No Drawings

ALKYLTHIOALKANOYLOXYALKYL AND ALKYLTHIOALKYL SUBSTITUTED BIS-HYDANTOIN COMPOUNDS

This is a Continuation of application Ser. No. 668,879 filed on Mar. 22, 1976, now abandoned.

BACKGROUND OF THE INVENTION

The present invention pertains to alkylthioalkanoyloxyalkyl and alkylthioalkyl derivatives of N-heterocyclic moieties and to compositions which are stabilized by these derivatives against the deleterious effects of heat and oxygen and against discoloration.

Of particular interest are polyolefin resin compositions containing said derivatives which are stabilized against thermal aging and light induced degradation. Polyolefin resins have inherently good mechanical and physical properties and are useful as resin substrates for molded articles, films and fibers. Other resins of particular interest include thermoplastic elastomers, ABS resins, polystyrene, and other hydrocarbon polymers.

In an attempt to permit these resins to exhibit the full measure of their inherent properties, it has been customary to add one or more stabilizers to the resins to overcome their susceptibility to oxidative and thermal degradation.

Phenolic antioxidants have long been used in the art as such stabilizers with varying degrees of success as seen in U.S. Pat. No. 3,285,855. It was shown in U.S. Pat. No. 2,956,982 that the dialkyl esters of β-thiodipropionic acid were also effective stabilizers for polyolefin resins. The combination of a lesser amount of a phenolic antioxidant with a small quantity of a dialkyl β-thiodipropionate was found to have a synergistic effect on the level of stabilization of such compositions superior to the use either of the phenolic antioxidant alone or the dialkyl β-thiodipropionate alone at the given concentration, (U.S. Pat. No. 3,285,855).

Other sulfur containing compounds have been discovered which also exhibit synergistic stabilization effects in combination with phenolic antioxidants in polyolefin compositions. These include the dialkyl alkylthiosuccinates (U.S. Pat. No. 3,345,327); the thiodialkanoate polyesters (U.S. Pat. No. 3,157,517 and U.S. Pat. No. 3,378,516); the derivatives of N',N",N'''-tris(3-mercaptopropionyl)-hexahydros-triazine (U.S. Pat. No. 3,538,092); the pentaerythritol or trimethylolpropane esters of alkylthioalkanoic acids (U.S. Pat. No. 3,629,194 and U.S. Pat. No. 3,758,549); and the 2,4,6-tris(alkylthioalkylthio)-1,3,5-triazines (U.S. Pat. No. 3,652,561).

While all of these materials exhibit useful synergistic stabilization effects in the presence of phenolic antioxidants in polyolefin or other hydrocarbon systems which are subject to oxidative and/or thermal deterioration, the dialkyl β-thiodipropionates (particularly the dilauryl and especially the distearyl esters) have become the thiosynergists of choice in the art enjoying widespread use.

DETAILS OF THE DISCLOSURE

The present invention pertains to alkylthioalkanoyloxyalkyl and alkylthioalkyl derivatives of N-heterocyclic moieties and to compositions which are stabilized by these sulfur compounds.

More particularly, this invention relates to compounds of the formula

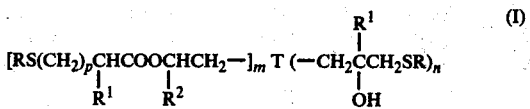

wherein
R is alkyl of 1 to 30 carbon atoms or cycloalkyl of 5 to 12 carbon atoms,
p is 0, 1 or 2,
$R^1$ is hydrogen or methyl,
$R^2$ is hydrogen, methyl or ethyl,
m is an integer from 0 to 3,
n is an integer from 0 to 3, with the proviso that the sum of m + n must be from 1 to 3, and
T is derived from an N-heterocyclic moiety and has the radical structure

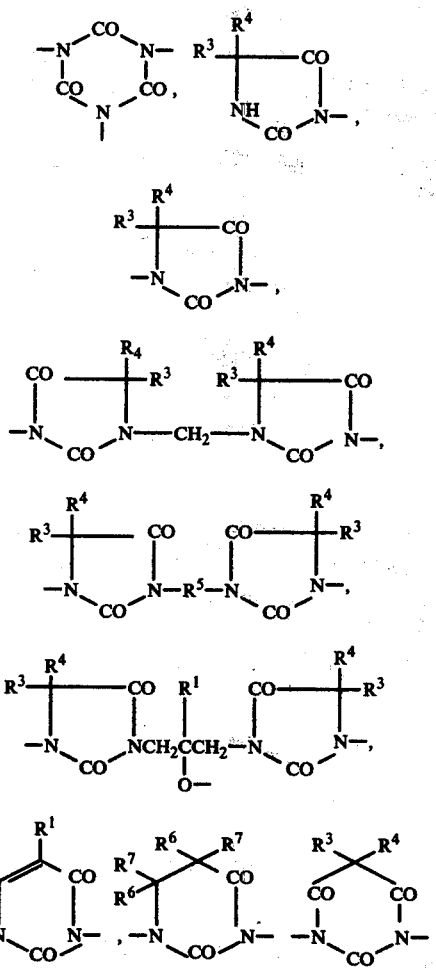

wherein
$R^1$ is hydrogen or methyl,
$R^3$ and $R^4$ are independently alkyl of 1 to 6 carbon atoms or together $R^3$ and $R^4$ are pentamethylene,
$R^5$ is alkylene of 1 to 12 carbon atoms or 3-oxapentamethylene,
$R^6$ and $R^7$ are independently hydrogen or alkyl of 1 to 4 carbon atoms.

Illustrative of the groups embraced by this invention are the following.

The R groups can be alkyl of 1 to 30 carbon atoms such as methyl, isopropyl, n-butyl, tert-amyl, n-octyl, n-dodecyl, tert-tridecyl, n-octadecyl and n-triacontyl. Embraced within these R groups are both straight and branched chain alkyl. R can also be cycloalkyl of 5 to 12 carbon atoms such as cyclopentyl, cyclohexyl, cyclooctyl and cyclododecyl.

Preferably R is alkyl of 1 to 18 carbon atoms or cyclohexyl, and most preferably R is alkyl of 12 to 18 carbon atoms.

$p$ can be 0, 1 or 2, but preferably $p$ is 0 or 1, and most preferably $p$ is 1.

$R^1$ can be hydrogen or methyl, but $R^1$ is preferably hydrogen.

$R^2$ is hydrogen, methyl or ethyl. Preferably $R^2$ is hydrogen or methyl and most preferably $R^2$ is hydrogen.

$m$ is an integer from 0 to 3, but $m$ is preferably 1 to 3 and $n$ is 0, and most preferably $m$ is 2 or 3 and $n$ is 0.

$n$ likewise is an integer from 0 to 3. Preferably $n$ is 1 to 3 and $m$ is 0, and most preferably $n$ is 2 or 3 and $m$ is 0.

The proviso that the sum of $m + n$ must be from 1 to 3 indicates that at least one sulfur containing group must be substituted on the T radical according to the present invention.

Preferably T is substituted by either one or more of the

groups or by one or more of the

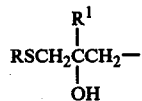

groups rather than by a combination of the two groups.

T is the radical derived from an N-heterocyclic moiety which may also be additionally substituted as seen from the structures given above. The

or

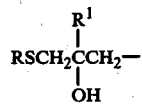

group is usually substituted on an heterocyclic nitrogen atom, but in the case of one T radical

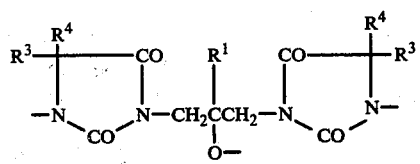

substitution also occurs on the oxygen atom on the bridge group between the two hydantoin moieties.

T represents the radicals from a variety of N-heterocyclic moieties including isocyanurates, substituted hydantoin, substituted bis-hydantoins with various bridging groups, substituted uracils, substituted 5,6-dihydrouracils and substituted barbituric acids.

Preferably T represents

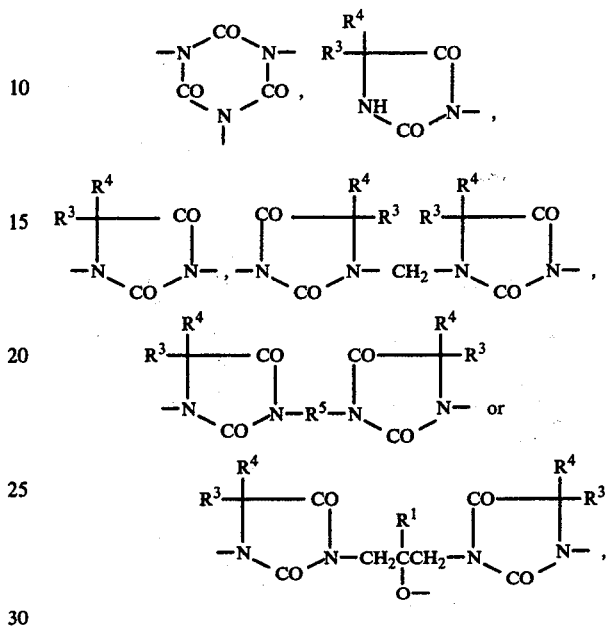

Preferably $R^3$ and $R^4$ are independently alkyl of 1 to 4 carbon atoms, and most preferably $R^3$ and $R^4$ are methyl.

Preferably $R^5$ is alkylene of 1 to 6 carbon atoms or 3-oxapentamethylene.

Preferably $R^1$ is hydrogen.

Most preferably T is

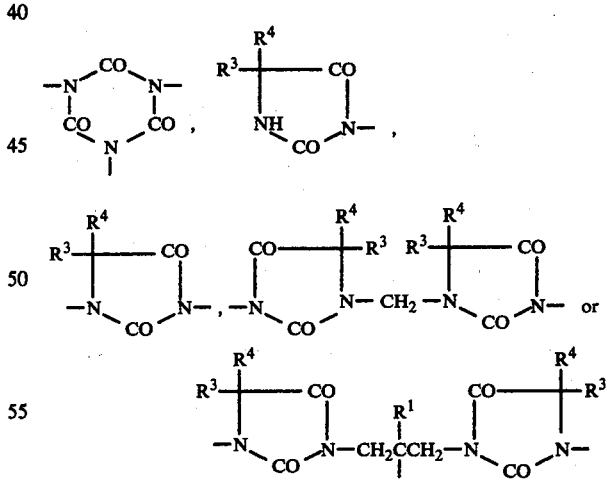

where $R^1$ is hydrogen and $R^3$ and $R^4$ are methyl.

Particularly preferred embodiments of the instant invention are the tris isocyanurates of the formula

wherein

R is alkyl of 12 to 18 carbon atoms, and T is

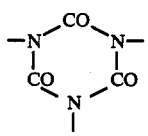

The compounds of this invention may be conveniently prepared by one of several different general methods.

R, $R^1$, $R^2$, $R^3$, $R^4$, $R^5$, T, m and n in all the preparative methods outlined below are as previously defined.

1. ESTERIFICATION

This method involves reacting an alkylthioalkanoic acid with hydroxyalkyl N-heterocyclic moiety using an acid catalyst, such as toluene sulfonic acid to give the desired ester by direct esterification.

Where p is 2, the alkylthioalkanoic acid may be prepared by reacting a mercaptan with α-haloalkanoic acid under alkaline conditions. Halo is preferably chloro or bromo.

2. TRANSESTERIFICATION

This method is exemplified in detail in Example 1. The method involves reacting a lower alkyl alkylthioalkanoate with a hydroxyalkyl N-heterocyclic moiety using typical transesterification catalysts such as sodium methylate, dibutyl tin oxide, lithium hydride and the like.

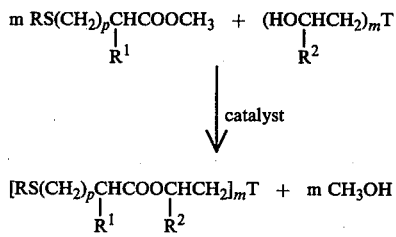

3. OPENING OF OXIRANE RING

This method is particularly exemplified in Examples 2 and 3. It involves reacting a mercaptan with an N-heterocyclic moiety having pendant oxirane rings in the presence of a basic catalyst such as sodium methoxide.

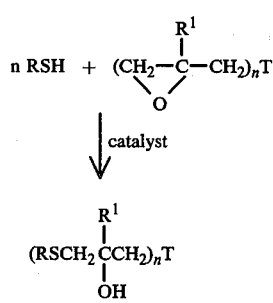

4. ADDITION OF MERCAPTAN TO DOUBLE BOND

The method is shown in detail in Examples 4–6, and involves the addition of a mercaptan to an N-heterocyclic moiety containing pendant groups having activated double bonds therein in the presence of a basic catalyst such as sodium methoxide.

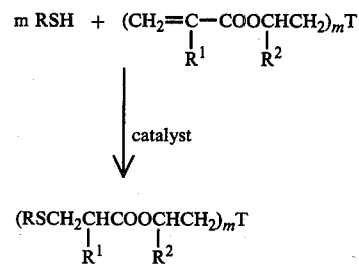

(This procedure is used where p is 1 in formula I)

While many of the intermediates used to prepare the compounds of this invention are items of commerce, the key intermediates required for making the compounds of this invention may be prepared as follows:

a. Where p is 1, the lower alkyl alkylthioalkanoates are prepared by reacting a mercaptan with a lower alkyl (preferably methyl) acrylate or methacrylate according to the method of C. D. Hurd et al, J. Amer. Chem. Soc., 69, 2332 (1947) and J. R. Stephens et. al, ibid, 73, 4050 (1951).

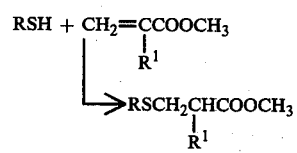

Where p is 0, the lower alkyl alkylthioacetates are prepared by reacting a mercaptan with a lower alkyl (preferably methyl) chloroacetate in the presence of alkaline catalyst.

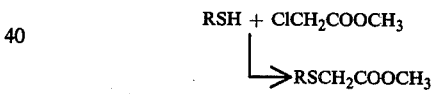

b. The N-heterocyclic moieties containing pendant hydroxyalkyl groups are prepared accordingly to the teachings of U.S. Pat. Nos. 2,381,121 and 3,629,263 by reaction of an N-heterocyclic moiety containing a replaceable hydrogen atom with an oxirane.

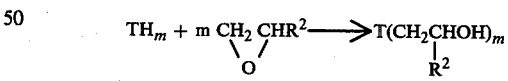

c. The N-heterocyclic moieties containing pendant oxirane rings are prepared by the teachings of Swiss Pat. No. 488,729, U.S. Pat. Nos. 3,592,823 and 3,821,243 by reacting an N-heterocyclic moiety containing a replaceable hydrogen atom with an epichlorohydrin in the presence of alkali.

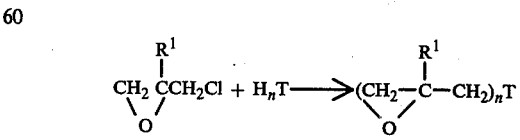

d. The particular N-heterocyclic moieties of use in this invention are prepared by several routes as seen below.

The 1,1-methylene bis-hydantoins are prepared by reacting the mono-hydantoin with formaldehyde as seen in U.S. Pat. No. 3,793,248.

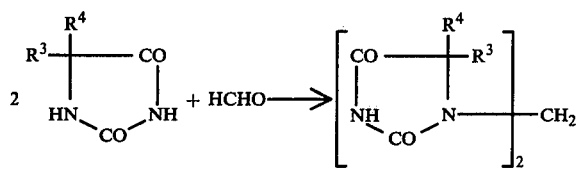

The N-heterocyclic moieties containing pendant groups having activated double bonds therein are prepared by reacting the N-heterocyclic moieties containing pendant hydroxyalkyl groups with acrylic or methacrylic acid in the presence of an acid catalyst according to the teachings of U.S. Pat. Nos. 3,808,226 and 3,852,302.

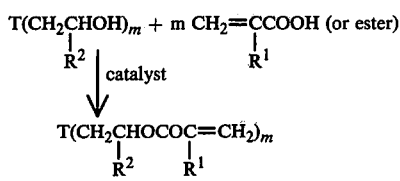

The 3,3-alkylene or oxaalkylene bis-hydantoins are prepared by reacting the mono-hydantoin with an alkylene (or oxaalkylene) dihalide, preferably chloride or bromide, in the presence of alkali according to the teachings of U.S. Pat. Nos. 3,296,208 and 3,542,803.

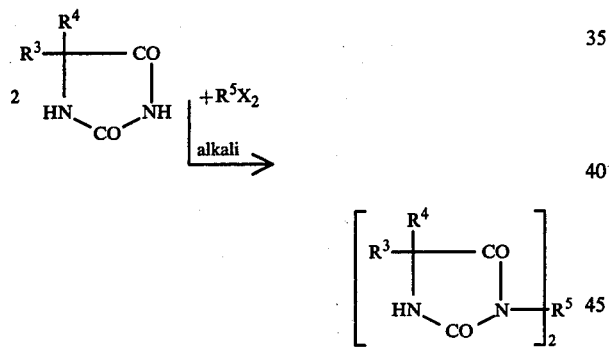

X = chlorine or bromine

The alkylthioalkanoyloxyalkyl and alkylthioalkyl derivatives of N-heterocyclic moieties of the present invention have as their characteristic property the ability to vastly improve the effect of numerous other compounds which are used as stabilizers for organic material normally subject to thermal and oxidative deterioration. Thus while the compounds of the present invention may be considered as stabilizers in their own right, their properties are such that they would be more conventionally classified as "synergists" in that when combined with known stabilizers, they exhibit the ability to increase stabilization to a degree far exceeding that which would be expected from the additive properties of the individual components.

The instant isocyanurates are particularly effective in preventing the deterioration of organic substrates in combination with various phenolic antioxidants.

The compositions of matter of this invention which are stabilized against deterioration comprise a polymer normally subject to deterioration containing from about 0.005% to 5% by weight of the polymer of the compounds of formula I. Organic materials such as, for example, the following polymers, can be stabilized using the compounds of the formula I.

1. Polymers which are derived from hydrocarbons with single or double unsaturation, such as polyolefins, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylenepropylene copolymers, propylene-butene-1 copolymers, propyleneisobutylene copolymers, styrene-butadiene copolymers and terpolymers of ethylene and propylene with a diene, such as, for example, hexadiene, dicyclopentadiene or ethylidene-norbornene; mixtures of above mentioned homopolymers, such as for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-14-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers such as cellulose, rubber, proteins and their polymer-homologously chemically modified derivatives, such as cellulose acetates, cellulose propionates and cellulose butyrates, or the cellulose ethers, such as methylcellulose.

17. High molecular monomeric substances, for example, mineral oils, animal and vegetable fats, oils and waxes, or oils, waxes and fats based on synthetic esters.

The compounds of this invention are particularly useful for the protection of polyolefins, for instance, polyethylene, polypropylene, poly(butene-1), poly(pentene-1), poly(3-methylbutene-1), poly(4-methylpentene-1), various ethylene-propylene copolymers and the like.

In general, the stabilizers of this invention are employed from about 0.01 to about 5% by weight of the stabilized composition, although this will vary with the particular substrate and application. An advantageous range is from about 0.05 to about 2%, and especially 0.1 to about 1%.

For addition to polymeric substrates, the stabilizers can be blended before polymerization or after polymerization, during the usual processing operations, for example, by hot-milling, the composition then being extruded, pressed, blow-molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface or films, fabrics, filaments or the like to provide effective stabilization. Where the polymer is prepared from a liquid monomer as in the case of styrene, the stabilizer may be dispersed or dissolved in the monomer prior to polymerization or curing.

In the case of crosslinked polyethylene, the compounds are added before the crosslinking.

The following may be mentioned as examples of further additives with which the compounds of the formula I can be co-employed:

1. ANTIOXIDANTS 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol, 2,6-dioctadecyl-4-methylphenol, 2,6-di-tert-butyl-4-butylphenol.

1.2 Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxyanisole, tris-(3,5-di-tert.-butyl-4-hydroxyphenyl)-phosphite, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6'di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)butane, 1,1-bis-(5-tert.-butyl-4-hydroxy-2-methylphenyl)-butane, 2,2-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5 O-, N- and S-benzyl compounds, such as, for example, 3,5,3'5'-tetra-tert.-butyl-4,4'-dihydroxydibenzyl ether, 4-hydroxy-3,5-dimethylbenzyl-mercaptoacetic acid octadecyl ester, tris(3,5-di-tert.-butyl-4-hydroxybenzyl)-amine and bis-(4-tert.-butyl-3-hydroxy-2,6-dimethylbenzyl)-dithioterephthalate.

1.6 Hydroxybenzylated malonic esters, such as, for example, 2,2-bis-(3,5-di-tert.-butyl-2-hydroxybenzyl)-malonic acid dioctadecyl ester, 2-(3-tert.-butyl-4-hydroxy-5-methylbenzyl)-malonic acid dioctadecyl ester, 2,2-bis-(3,5-di-tert.-butyl-4-hydroxybenzyl)-malonic acid didodecylmercaptoethyl-ester and 2,2-bis-(3,5-di-tert.-butyl-4-hydroxybenzyl)-malonic acid di-[4-(1,1,3,3-tetramethylbutyl)-phenyl]-ester.

1.7 Hydroxybenzyl-aromatics, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example, 2,4-bis-octylmercapto-6-(3,5,di-tert.-butyl-4-hydroxy-anilino)-s-triazine, 2-octylmercapto-4,6-bis-(3,5-di-tert-butyl-4-hydroxy-anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)-isocyanurate.

1.9 Amides of β-(3,5-di-tert.-butyl-4-hydroxyphenyl)-propionic acid, such as, for example, 1,3,5-tris-(3,5-di-tert.butyl-4-hydroxyphenyl-propionyl-hexahydro-s-triazine and N,N'-di-(3,5-di-tert.-butyl-4-hydroxyphenyl-priopionyl)-hexamethylenediamine.

1.10 Esters of β-(3,5-di-tert.-butyl-4-hydroxyphenyl-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thiapentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.11 Esters of β-(5-tert.-butyl-4-hydroxy-3-methylphenyl propionic acid with monohydric or polyhydric alcohols, such as, for example, methanol, ethanol, octadecanol, 1,6-hexanediol, 1,9- nonanediol, ethylene glycol, 1,2-propanediol, diethylene glycol, thiodiethylene glycol, neopentylglycol, pentaerythritol, 3,thia-undecanol, 3-thiapentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.12 Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, 3-thia-heneicosanol-1, trimethyl hexane-diol, trimethylolethane, trimethylolpropane, tris-hydroxyethyl isocyanurate and 4-hydroxymethyl-1-phospha-2,6,7-trioxabicyclo-[2,2,2]octane.

1.13 Acylaminophenols, such as, for example, N-(3,5,-di-tert.-butyl-4-hydroxyphenyl)stearic acid amide, N,N'-di-(3,5-di-tert-butyl-4-hydroxyphenyl)-thiobis-acetamide and thiophosphoric acid O,O-diethyl ester 3,5-di-tert.-butyl-4-hydroxy anilide.

1.14 Benzylphosphonates, such as, for example, 3,5-di-tert.-butyl-4-hydroxybenzyl-phosphonic acid dimethyl ester, 3,5-di-tert.-butyl-4-hydroxybenzyl-phosphonic acid diethyl ester, 3,5-di-tert.-butyl-4-hydroxybenzyl-phosphonic acid dioctadecyl ester and 5-tert.-butyl-4-hydroxy-3-methylbenzyl-phosphonic acid diotadecyl ester.

Although the compounds of this invention are to some degree effective as thermal stabilizers, if the processing of the polymer is carried out at high temperatures, it is advantageous to incorporate additional antioxidants.

In most applications, it is desirable to incorporate into the the resin composition, sufficient thermal antioxidants to protect the plastic against thermal and oxidative degradation. The amount of antioxidant required will be from about 0.005% to 5% and preferably from 0.01% to 2% by weight.

The best results have been obtained with the preferred class of thermal antioxidants, the hindered phenols. These compounds have been found to provide the best thermal stabilization with the least discoloration in the compositions of the invention. Among this preferred class of thermal antioxidants may be mentioned the following:

di-n-octadecyl 3,5-di-butyl-4-hydroxybenzyl-malonate
2,6-di-t-butyl-4-methylphenol
2,2'-methylene-bis(6-t-butyl-4-methylphenol)
2,6-di-t-butylhydroquinone
octadecyl (3,5-di-t-butyl-4-hydroxybenzylthio)-acetate
1,1,3-tris(3-t-butyl-6-methyl-4-hydroxyphenyl)-butane
1,4-bis(3,5-di-t-butyl-4-hydroxybenzyl)-2,3,5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl β-(3,5-di-t-butyl-4-hydroxyphenyl)-propionate
2,4,6-tris(3,5-di-tert-butyl-4-hydroxybenzyl) isocyanurate
di-n-dodecyl 6-tert-butyl-2,3-dimethyl-4-hydroxybenzyl-phosphonate
stearamido N,N-bis-[ethylene 3-(3,5,di-t-butyl-4-hydroxyphenyl)propionate]
1,2-propylene glycol bis[3-(3,5-di-t-butyl-4-hydroxyphenyl)propionate]
pentaerythritol tetrakis-[3-(3,5-di-t-butyl-4-hydroxyphenyl)propionate
dioctadecyl 3,5-di-t-butyl-4-hydroxybenzylphosphonate
di-n-octadecyl 1-(3,5-di-t-butyl-4-hydroxyphenyl)-ethanephosphonate.

The above phenolic hydrocarbon stabilizers are known and many are commercially available.

The above exemplified antioxidants and other related antioxidants which are incorporated herein by reference, are disclosed in greater detail in the following patents:

Netherlands Pat. Specification No. 67/1119, issued Feb. 19, 1968; Netherlands Pat. Specification No. 68/03498, issued Sept. 18, 1968; U.S. Pat. Nos. 3,255,191; 3,330,859; 3,644,482, 3,281,505; 3,531,483; 3,285,855; 3,364,250; 3,368,997; 3,357,944 and 3,758,549.

In addition to one or more of the above phenolic stabilizers, it is often advantageous to employ other additives such as ultraviolet light absorbers, e.g., 2-hydroxy-4-methoxybenzophenone, 2-(2'-hydroxy-5'-methylphenyl)benzotriazole, etc.; various phosphite compounds such as trioctylphosphite, dilaurylphosphite, tris(nonylphenyl)phosphite and the like. Such two, three or four component systems, when including a compound of the present invention, exhibit far superior properties to the additive properties of the individual components.

Other materials often added to such organic materials, depending upon the substrate, include pour-point depressants, corrosion and rust inhibitors, metal deactivators, demulsifiers, antifoam agents, carbon black, accelerators, plasticizers, color stabilizers, heat stabilizers, dyes, pigments, lubricants, emulsifiers, fillers, asbestos, kaolin, talc, glass fibers, optical brighteners, flameproofing agents, antistatic agents, dispersing agents, antiozonants, metal chelating agents, dyesites, chemicals used in rubber compounding and the like.

The alkyl alkylthioalkanoic acid esters of the present invention are preferably used in a concentration of from 0.005% to about 5% by weight of the total composition together with one or more of the above phenolic antioxidants, one or more ultraviolet light absorbers and/or one or more of the above phosphite compounds. These are particularly useful in synthetic organic polymeric substances such as polypropylene, polyethylene, polystyrene and the like to protect such substances from deterioration both during use and during processing such as milling polypropylene or blow molding polyethylene. The compounds of the present invention exhibit superior compatibility in diverse substrates with little or no odor formation.

They are particularly useful in organic polymeric fibers because of their extraction resistance and low volatility.

The compositions containing a compound of formula I show better resistance to discoloration, particularly at elevated temperatures compared to thiosynergists of the prior art.

It is also contemplated that compositions containing a compound of formula I in the presence of a phenolic antioxidant will exhibit superior resistance to discoloration in the presence of alkaline detergents.

The following examples are presented for the purpose of illustration only and are not to be construed to limit the nature or scope of the instant invention in any manner whatsoever.

EXAMPLE 1

Tris[2-(3-n-dodecylthiopropionyloxy)ethyl] Isocyanurate (a) To a 300 ml. 3-necked flask equipped with a thermometer, nitrogen inlet tube, stirrer and condenser with drying tube were added under nitrogen 15.7 grams (0.06 mole) of tris(2-hydroxyethyl)isocyanurate (THEIC), 57.1 grams (0.198 mole) of methyl 3-n-dodecylthiopropionate and 2.23 grams (0.009 mole) of dibutyl tin oxide catalyst. The reaction mixture was slowly heated to 135° C. and kept at that temperature for 3 hours. A vacuum of 20–25 mm was then applied at 130° C. for one hour. On cooling to about 80° C. the resulting solution solidified to a white, waxy solid.

A thin layer chromatographic (TLC) analysis of the crude solid indicated a minor amount of the methyl 3-n-dodecylthiopropionate was present. The crude solid was twice recrystallized from heptane to give 42 grams (68% yield) of a white crystals melting at 71°–73° C. (Compound 1).

Elemental Analysis for $C_{54}H_{99}N_3O_9S_3$; Calculated: C, 62.93; H, 9.68; N, 4.08; S, 9.33. Found: C, 63.06; H, 9.67; N, 4.01; S, 9.17.

(b) Methyl 3-n-dodecylthiopropionate was made by adding methyl acrylate to a mixture of n-dodecyl mercaptan and sodium methoxide according to the procedure of J. R. Stephens et al, J. Am. Chem. Soc., 73, 4050 (1951).

By essentially following the procedure of (b), but substituting for n-dodecyl mercaptan an equivalent amount of the following mercaptans:
(a) ethyl mercaptan
(b) n-hexyl mercaptan
(c) n-octyl mercaptan
(d) n-decyl mercaptan
(e) tert-dodecyl mercaptan
(f) n-octadecyl mercaptan
(g) tridecyl mercaptan
(h) n-eicosyl mercaptan
(i) n-tricontyl mercaptan
(j) cyclohexyl mercaptan
there is respectively obtained
(a) methyl 3-ethylthiopropionate
(b) methyl 3-n-hexylthiopropionate
(c) methyl 3-n-octylthiopropionate
(d) methyl 3-n-decylthiopropionate
(e) methyl 3-tert-dodecylthiopropionate
(f) methyl 3-n-octadecylthiopropionate
(g) methyl 3-tridecylthiopropionate
(h) methyl 3-n-eicosylthiopropionate
(i) methyl 3-n-tricontylthiopropionate
(j) methyl 3-cyclohexylthiopropionate Substitution of an equivalent amount of any one of these methyl propionate esters for the methyl 3-n-dodecylthiopropionate in the procedures of (a) leads to the corresponding isocyanurates below:

(a) tris[2-(3-ethylthiopropionyloxy)ethyl] isocyanurate
(b) tris[2-(3-n-hexylthiopropionyloxy)ethyl] isocyanurate
(c) tris[2-(3-n-octylthiopropionyloxy)ethyl] isocyanurate
(d) tris[2-(3-n-decylthiopropionyloxy)ethyl] isocyanurate
(e) tris[2-(3-tert-dodecylthiopropionyloxy)-ethyl] isocyanurate
(f) tris[2-(3-n-octadecylthiopropionyloxy)-ethyl] isocyanurate
(g) tris[2-(3-tridecylthiopropionyloxy)ethyl] isocyanurate
(h) tris[2-(3-n-eicosylthiopropionyloxy)ethyl] isocyanurate
(i) tris[2-(3-n-triacontylthiopropionyloxy)ethyl] isocyanurate
(j) tris[2-(3-cyclohexylthiopropionyloxy)ethyl] isocyanurate

EXAMPLE 1a

Tris[2-(n-dodecylthioacetoxy)ethyl] isocyanurate

When in the procedure of Example 1 the methyl 3-n-dodecylthiopropionate is substituted by an equivalent amount of methyl n-dodecylthioacetate, the above named product is obtained.

Methyl n-dodecylthioacetate is prepared by the reaction of n-dodecyl mercaptan with methyl chloroacetate in the presence of an alkaline catalyst. Substitution of any of the mercaptans listed in Example 1 for the n-dodecyl mercaptan results in the preparation of the corresponding methyl alkylthioacetate. Substitution of another methyl alkylthioacetate for methyl n-dodecylthioacetate in the reaction with tris(2-hydroxyethyl)isocyanurate in Example 1a produces the corresponding tris[2-(alkylthioacetoxy)-ethyl] isocyanurate.

EXAMPLE 1b

Tris[2-(4-n-dodecylthiobutylryloxy)ethyl] Isocyanurate

When in the procedure of Example 1 the methyl 3-n-dodecylthiopropionate is replaced by an equivalent amount of methyl 4-n-dodecylthiobutyrate, the above named product is obtained.

Alternatively, the above named product is preby the direct esterification of 4-n-dodecylthiobutyric acid with tris(2-hydroxyethyl) isocyanurate in benzene in the presence of the acid catalyst, toluene sulfonic acid.

4-n-Dodecylthiobutyric acid or its methyl ester is prepared by reaction of n-dodecyl mercaptan and γ-bromoalkanoic acid or ester under alkaline conditions. Substitution of any of the mercaptans listed in Example 1 for the n-dodecyl mercaptan results in the corresponding 4-alkylthiobutyric acid or ester and thereon as shown above to the corresponding tris[2-(4-alkylthiobutyryloxy) ethyl] isocyanurate.

EXAMPLE 2

3-(3-n-Dodecylthio-2-hydroxypropyl)-5,5-dimethylhydantoin (a) To a 3-necked 300 ml flask fitted with a stirrer, thermometer, nitrogen inlet tube and condenser with drying tube were added 18.4 grams (0.1 mole) of 3-glycidyl-5,5-dimethylhydantoin, 20.2 grams (0.1 mole) of n-dodecyl mercaptan and 100 ml of ethanol. To the resulting water-white solution was added 108 milligrams (2 m mole or 2 mol percent based on the mercaptan) sodium methoxide. The mixture was stirred at ambient termperature for 45 hours and then for 4.5 hours at 55° C. A copious amount of white precipitate formed at ambient temperature, but redissolved when the mixture was heated to 55° C. Vapor phase chromatography indicated a trace of unreacted mercaptan, but a preponderance of the desired substituted hydantoin named above. The product was isolated by cooling the mixture, separating the product by filtration and recrystallizing the crude product from ethanol to give 14.1 grams (37% yield) of a white solid melting at 95°–97° C. (Compound 2)

Elemental Analysis for $C_{20}H_{38}N_2O_3S$: Calculated: C, 62.14; H, 9.91; N, 7.24; S, 8.29. Found: C, 61.97; H, 10.02; N, 7.37; S, 8.38.

(b) 3-glycidyl-5,5-dimethylhydantoin may be prepared by reaction of 5,5-dimethylhydantoin with epichlorohydrin according to Swiss Pat. No. 488,729.

EXAMPLE 3

1,1'-Methylene-bis[3-(3-n-dodecylthio-2-hydroxypropyl)-5,5-dimethylhydantoin]

(a) Using the general procedure described in Example 2, a solution of 25.4 grams (0.125 mole) of n-dodecyl mercaptan and 135 milligrams (2.5 m. moles) of sodium methoxide was prepared in 125 ml of ethanol. To this solution was then added 23.85 grams (0.0625 mole) of 1,1'-methylene-bis(3-glycidyl-5,5-dimethylhydantoin). The resulting solution was then stirred for 20 hours at 55° C. The solution was filtered and then heated under vacuum at 70° C./20 mm and finally distilled at 80° C./2 mm to give 45.6 grams (92% yield) of a white wax with a melting point of 49°–51° C. (Compound 3).

Elemental Analysis for $C_{41}H_{76}N_4O_6S_2$: Calculated: C, 62.71; H, 9.76; N, 7.14; S, 8.17. Found: C, 62.68; H, 9.77; N, 6.95; S, 8.21.

(b) 1,1'-Methylene-bis[3-glycidyl-5,5-dimethylhydantoin] is prepared by the reaction of epichlorohydrin and 1,1'-methylene-bis[5,5-dimethylhydantoin] according to Example 1 of U.S. Pat. No. 3,592,923. 1,1'-Methylene-bis[5,5-dimethylhydantoin] is prepared by the general procedure of Example I of U.S. Pat. No. 3,793,248 using paraformaldehyde and 5,5-dimethylhydantoin.

EXAMPLE 4

1,3-Bis[2-(3-n-dodecylthiopropionyloxy)ethyl]-5,5-dimethylhydantoin (a) To a 200 ml 3-necked flask fitted with an addition funnel, thermometer, nitrogen inlet tube, drying tube and magnetic stirrer was added under nitrogen 12.65 grams (0.0625 mole) of n-dodecyl mercaptan and then 135 milligrams (2.5 millimole) of sodium methoxide. The mixture was cooled to 10° C. and 8.1 grams (0.025 mole) of 1,3-bis(2-acryloyloxyethyl)-5,5-dimethylhydantoin in 10 ml of tetrahydrofuran was added over a 15 minute period. The exothermic reaction caused the temperature to rise to 20° C. The reaction mixture was then stirred for 20 hours at 25° C. To the slightly turbid solution was added 0.5 ml of acetic acid. The solution was then filtered and heated under vacuum at 75° C./20 mm for 30 minutes. The crude heavy straw colored oil (19 grams) was then topped off at 200° C./10μ to give 11.2 grams (62% yield) of a goldenbrown oil. (Compound 4).

Elemental Analysis for $C_{39}H_{72}N_2O_6S_2$: Calculated: C, 62.24; H, 9.95; N, 3.84; S, 8.80. Found: C, 62.78; H, 10.06; N, 3.83; S, 8.16.

(b) 1,3-Bis(2-acryloyloxyethyl)-5,5-dimethylhydantoin is prepared by reaction of acrylic acid and 1,3-bis(2-hydroxyethyl)-5,5-dimethylhydantoin according to Example 4 of U.S. Pat. No. 3,852,302. 1,3-Bis(2-hydroxyethyl)-5,5-dimethylhydantoin is prepared by the reaction of 5,5-dimethylhydantoin and ethylene oxide according to Example C of U.S. Pat. No. 3,629,263.

EXAMPLE 5

1,1'-Methylene-bis-[3-(3-n-dodecylthiopropionyloxy-2-hydroxypropyl)-5,5-dimethylhydantoin]

(a) Following the general procedure described in Example 4, to a mixture of 12.65 grams (0.0625 mole) of n-dodecyl mercaptan and 135 milligrams (2.5 millimoles) of sodium methoxide cooled to 10° C. was added over a 15 minute period 13.1 grams (0.025 mole) of 1,1'-methylene-bis-[3-(3-acryloyloxy-2-hydroxypropyl)-5,5-dimethylhydantoin] in 40 ml of tetrahydrofuran. The temperature rose to 22° C. due to the exothermic reaction. The resulting mixture was stirred at room temperature for 18 hours.

To the slightly turbid solution was added 0.5 ml of acetic acid. The resulting solution was filtered through filter-cel and then heated under vacuum at 70° C./20 mm to give 22 grams of a clear syrup. This syrup was then topped off at 200° C./10μ to give 14 grams (60% yield) of a brown gum. (Compound 5).

Elemental Analysis for $C_{47}H_{84}N_4O_{10}S_2$: Calculated: C, 60.74; H, 9.11; N, 6.03; S, 6.90. Found: C, 59.56; H, 8.69; N, 6.87; S, 5.77.

(b) 1,1'-Methylene-bis[3-(3-acryloyloxy-2-hydroxypropyl)-5,5-dimethylhydantoin] is prepared by the reaction of acrylic acid and 1,1'-methylene-bis[3-glycidyl-5,5-dimethylhydantoin], see preparation in Example 3b, according to Example 1 of U.S. Pat. No. 3,808,226.

EXAMPLE 6

3,3'-[2-(3-n-Dodecylthiopropionyloxy-2-hydroxypropoxy)]trimethylene-bis-[1-(3-n-dodecylthiopropionyloxy-2-hydroxypropyl)-5,5-dimethylhydantoin]

(a) Following the general procedure described in Example 4, to a mixture of 12.65 grams (0.0625 mole) of n-dodecyl mercaptan and 135 milligrams (2.5 milimoles) of sodium methoxide cooled to 10° C. was added over a 15-minute period 11.6 grams (0.013 mole) of 3,3'-[2-(3-acryloyloxy-2-hydroxypropoxy)]trimethylene-bis[1-(3-acryloyloxy-2-hydroxypropyl)-5,5-dimethylhydantoin] in 20 ml. of tetrahydrofuran. The temperature of the mixture rose to 25° C. due to the exothermic reaction. The resulting mixture was then stirred at room temperature for 16 hours.

To the slightly turbid solution was added 0.5 ml of acetic acid. The resulting mixture was filtered through filter-cel and then heated under vacuum at 70° C./20 mm to give 20 grams of a clear syrup. This syrup was then topped off at 200° C./10μ to give 15.1 grams (89% yield) of a golden brown gum. (Compound 6).

Elemental Analysis for $C_{67}H_{121}N_4O_{14}S_3$: Calculated: C, 61.76; H, 9.36; N, 4.30; S, 7.37. Found: C, 61.49; H, 9.34; N, 4.30; S, 6.94.

(b) 3,3'-[2-(3-Acryloyloxy-2-hydroxypropoxy)trimethylene]-bis[1-(3-acryloyloxy-2-hydroxypropyl)-5,5-dimethylhydantoin] is prepared according to the general procedure of Example 1, U.S. Pat. No. 3,808,226 wherein acrylic acid is reacted with the corresponding triglycidyl hydantoin compound, 3,3'-(2-glycidyloxy)-trimethylene-bis[1-glycidyl-5,5-dimethylhydantoin].

This latter compound is prepared by the reaction of epichlorohydrin and 3,3'-(2-hydroxy)trimethylene-bis[5,5-dimethylhydantoin] according to Example 1 of U.S. Pat. No. 3,821,243. This starting material may be prepared by reaction of 5,5-dimethylhydantoin and epichlorohydrin according to Example C of U.S. Pat. No. 3,821,243.

EXAMPLE 7

Tris[3-(n-dodecylthio)-2-hydroxypropyl] Isocyanurate

To a stirred solution of 88 grams (0.4 mole) of n-dodecyl mercaptan in 300 ml of 2B ethanol at room temperature under nitrogen and drying conditions was added 1.08 grams (0.02 mole) of sodium methoxide in one portion. After the methoxide dissolved, 39.63 grams (0.133 mole, 0.4 equivalents) of recrystallized triglycidyl isocyanurate was added. After 30 minutes, the mixture was a slightly turbid solution, and the resulting mixture was stirred at 55° C. for 20 hours. A heavy white precipitate came out of solution. The mixture was then diluted with another 300 ml of 2B ethanol, the temperature was raised to 75° C. The mixture again was a slightly turbid solution which was filtered hot. The product crystallized from the filtrate at room temperature and was collected in a yield of 78 grams. The product was then recrystallized from 2B alcohol to give a yield of 73 grams (72%) of white crystals melting at 94°–97° C. (Compound 7).

Elemental Analysis for $C_{48}H_{93}N_3O_6S_3$: Calculated: C, 63.74; H, 10.36; N, 4.64; S, 10.63. Found: C, 63.59; H, 9.87; N, 4.64; S, 10.65.

EXAMPLE 8

Unstabilized polypropylene powder (Hercules Profax 6501) was thoroughly blended with 0.3% by weight of the various thio derivatives of this invention and 0.1% by weight various phenolic antioxidants. The blended materials were then milled on a two-roll mill at 182° C. for 10 minutes, after which time the stabilized polypropylene was sheeted from the mill and allowed to cool.

The milled polypropylene sheets were then cut into pieces and pressed for 7 minutes on an hydraulic press at 218° C. on a hydraulic press at 275 psi (19.25 kg/cm$^2$) pressure and then transferred to a cold press the same pressure. Sample plaques of the resulting 25 mil (0.635 mm) sheet were tested for resistance to accelerated aging in a forced draft oven at 150° C. When the plaques showed the first sign of decomposition (e.g., cracking or brown edges), they were considered to have failed. The results are shown in Table I below:

TABLE I

| 150° C. Oven Aging of Polypropylene Plaques | |
|---|---|
| Percent Stabilizer | Hours to Failure |
| Unstabilized polypropylene | 3 |
| 0.3% distearyl β-thiodipropionate (DSTDP) | 100, 180 |
| 0.3% Compound 1 | 80 |
| 0.1% IRGANOX 1010* | 820 |
| 0.3% IRGANOX 1010 | 1170 |
| 0.1% IRGANOX 1010 plus 0.3% DSTDP | 1720 |
| 0.1% IRGANOX 1010 plus 0.3% Compound 1 | 3120 |
| 0.1% IRGANOX 1010 plus 0.3% Compound 2 | 980 |

TABLE I-continued

| 150° C. Oven Aging of Polypropylene Plaques | |
|---|---|
| Percent Stabilizer | Hours to Failure |
| 0.1% IRGANOX 1010 plus 0.3% Compound 4 | 2145 |
| 0.1% IRGANOX 1010 plus 0.3% Compound 5 | 1280 |
| 0.1% IRGANOX 1010 plus 0.3% Compound 6 | 1460 |

*IRGANOX 1010, neopentanetetrayl tetrakis[3,5-di-tert-butyl-4-hydroxyhydrocinnamate]

EXAMPLE 9

A quantity of SBR emulsion containing 100 g of rubber (500 ml of 20% SRB emulsion obtained from Texas U.S., as Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (1 mm) at 40°–45° C.

The dried rubber (25 g) is heated under nitrogen at 125° C. in a Brabender mixer and to this is added with mixing 1.25 g (0.5%) of 1,3,5-tri(3,5-di-t-butyl-4-hydroxybenzyl)-2,4,6-trimethylbenzene and 0.1% by weight of tris[2-(3-n-octadecylthiopropionyloxy)ethyl] isocyanurate.

Portions of the rubber composition are heated in a circulating air oven at 100° C. for up to 96 hours. The viscosity of a 0.5% toluene solution of aged and unaged rubber samples are determined at 25° C. Stabilizer effectiveness is judged by the percent retention of specific viscosity, color formation and gel content after oven aging. The stabilized rubber has better viscosity, color retention, and less gel content than the rubber which is unstabilized after oven aging.

Similar results are obtained when n-octadecyl 3-(3,5-di-t-butyl-4-hydroxyphenyl)propionate and tris[2-(3-n-octylthiopropionyloxy)ethyl] isocyanurate are used in place of the above mentioned stabilizers in the rubber composition.

EXAMPLE 10

A composition is prepared comprising linear polyethylene and 0.05% by weight of pentaerythritol tetrakis [3,(3,5-di-t-butyl-4-hydroxyphenyl)propionate] and 0.01% by weight of tris[2-(3-tert-dodecylthiopropionyloxy)ethyl] isocyanurate. The composition is injected molded into tensile bars which are placed in a circulating air oven at 120° C. In contrast to those molded from unstabilized linear polyethylene, tensile bars molded from the instant composition retain their tensile strength for substantially longer period.

EXAMPLE 11

Cyclohexene, freshly distilled is stabilized by the addition thereto of 0.05% by weight of 2,2'-methylene-bis(6-butyl-4-methylphenol) and 0.01% by weight of tris[2-(3-n-hexylthiopropionyloxy)ethyl] isocyanurate. The effectiveness of this stabilizer in cyclohexens is tested by the ASTM D 525-55 oxidation test. The unstabilized cyclohexene fails in shorter time as compared to the stabilized cyclohexene.

EXAMPLE 12

A stabilized high temperature lubricating oil is prepared by incorporating 2% weight of 4,4'-thiobis(2-t-butyl-5-methylphenol) and 0.5% by weight of tris[2-(3-n-decylthiopropionyloxy)ethyl] isocyanurate to the lubricant which comprises diisoamyl adipate. The stabilized composition is compared with the unstabilized lubricant by heating at 175° in the presence of air and metallic catalysts according to the test method described in Military Specification Mil-I-7808c. After 72 hours, the blank containing no stabilizer contains more sludge and has a greater viscosity than the stabilized lubricant.

EXAMPLE 13

A water-white, refined (U.S.P. grade) mineral oil (esso PRIMOL D) is stabilized and tested under the following test conditions.

A sample of the mineral oil (10 g) containing 0.1% by weight of di-n-octadecyl 3,5-di-t-butyl-4-hydroxybenzyl phosphonate and 0.3% of 3-(3-n-dodecylthio-2-hydroxypropyl)-5,5-dimethylhydantoin is placed in a Sligh type oxidation flask filled with oxygen at room temperature (25° C.) and atmospheric pressure. Thereafter, the flask is sealed to form a system having a mercury manometer which measures the pressure changes as oxygen is absorbed by the sample in the flask. The sample is then heated at 150° C. until the manometer registers a decrease of 300 mm Hg pressure within the flask with reference to the maximum pressure obtained at 150° C. Results of this test show the increase oxidation resistance for the sample containing the stabilizer.

EXAMPLE 14

High impact polystyrene resin containing elastomer (i.e., butadiene-styrene) is stabilized against loss of elongation properties by incorporation of 0.1% by weight of di-n-octadecyl (3-t-butyl-4-hydroxy-5-methylbenzylmalonate) and 0.1% by weight of 1,1'-methylene-bis[3-(3-n-dodecylthio-2-hydroxypropyl)-5,5-dimethylhydantoin]. Under the test conditions described below, the stabilized resin retains a higher percentage of its original elongation properties, whereas the unstabilized resin retains less elongation properties. A substantial improvement in stability is also noted when only 0.05% of the stabilizer is employed.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C. and a pressure of 2,000 psi (140 kg/cm²) into a sheet of uniform thickness of 0.635 mm (25 mil). The sheets are then cut into strips approximately 10.16 cm × 1.27 cm (4 × 0.5 inches). A portion of these strips is then measured for length of elongation in the Instron Tensile (Instron Engineering Corporation, Quincy, Massachusetts). The remaining portion of the strips is aged in a forced draft oven for 6 weeks at 75° C. and thereafter tested for elongation. The stabilized polystyrene resin has retained its elongation property much better than the unstabilized resin.

Similar results are obtained when an equivalent amount of the following stabilizer combinations are used in place of the above mentioned stabilizer combinations.

(a) 0.1% by weight 1,3-bis-[2-(3-n-dodecylthiopropionyloxy)ethyl]-5,5-dimethylhydantoin + 0.3% of 4,4'-butylidene-bis(2,6-di-t-butyl-phenol)

(b) 0.1% by weight of 1,1'-methylene-bis[3-(3-n-dodecylthiopropionyloxy-2-hydroxypropyl)-5,5-dimethylhydantoin] + 0.3% of 2,4-bis(n-octylthio)-6-(3,5-di-t-butyl-4-hydroxyanilino)-1,3,5-triazine (c) 0.1% by weight of 3,3'-[2-(3-n-dodecylthiopropionyloxy-2-hydroxypropoxy)]trimethylene-bis[1-(3-n-dodecylthiopropionyloxy-2-hydroxypropyl)-5,5-dimethylhydantoin] + 0.3% of 2,4-bis(3,5-di-t-butyl-hydroxyphenoxy-6-(n-octylthio)-1,2,3-triazine.

What is claimed is:

1. A compound of the formula

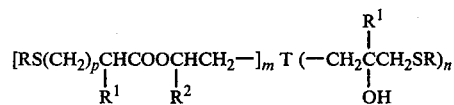

where $m$ is an integer from 0 to 2 and $n$ is an integer from 0 to 2, with the proviso that the sum of $m + n$ must be 2 when T is a radical of the structure

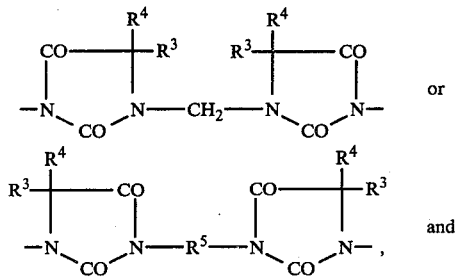

where $m$ is an integer from 0 to 3 and $n$ is an integer from 0 to 3, with the proviso that the sum of $m + n$ must be 3 when T is a radical of the structure

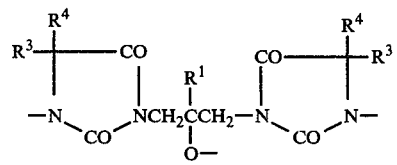

wherein

R is alkyl of 1 to 30 carbon atoms or cycloalkyl of 5 to 12 carbon atoms, $p$ is 0, 1 or 2, $R^1$ is hydrogen or methyl, $R^2$ is hydrogen, methyl or ethyl, $R^3$ and $R^4$ are independently alkyl of 1 to 6 carbon atoms or together $R^3$ and $R^4$ are pentamethylene, and $R^5$ is alkylene of 1 to 12 carbon atoms or 3-oxapentamethylene.

2. A compound according to claim 1 which is
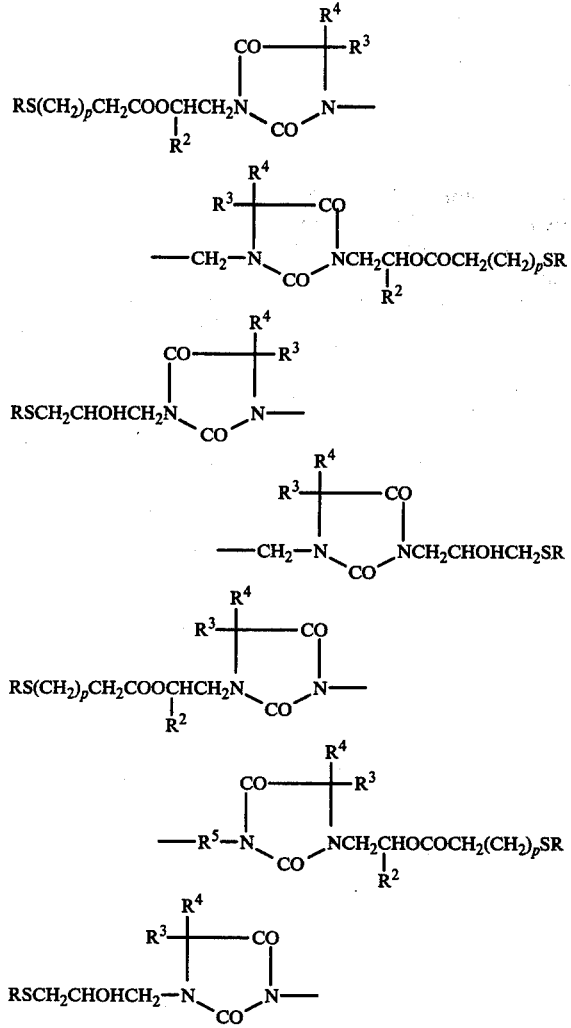
where
R is alkyl of 1 to 18 carbon atoms or cyclohexyl,
p is 0 or 1,
$R^2$ is hydrogen or methyl,
$R^3$ and $R^4$ are independently alkyl of 1 to 4 carbon atoms, and
$R^5$ is alkylene of 1 to 6 carbon atoms or 3-oxapentamethylene.
3. A compound according to claim 1 which is
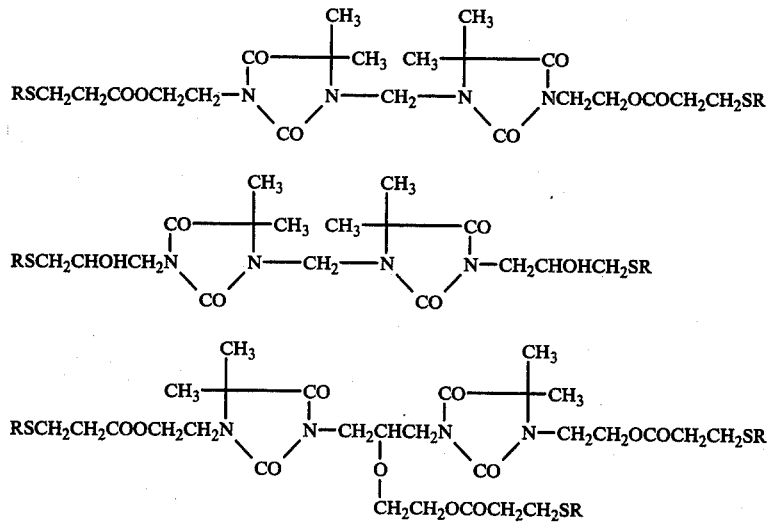
or -continued

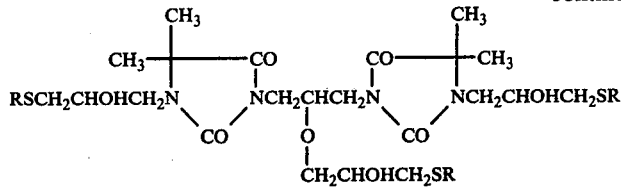

where R is alkyl of 12 to 18 carbon atoms.

4. The compound according to claim 1 which is 1,1'-methylene-bis[3-(3-n-dodecylthio-2-hydroxypropyl)-5,5-dimethylhydantoin].

5. The compound according to claim 1 which is 1,1'-methylene-bis[3-(3-n-dodecylthiopropionyloxy-2-hydroxypropyl)-5,5-dimethylhydantoin].

6. The compound according to claim 1 which is 3,3'-[2-(3-n-dodecylthiopropionyloxy-2-hydroxypropoxy)]-trimethylene-bis-[1-(3-n-dodecylthiopropionyloxy-2-hydroxypropyl)-5,5-dimethylhydantoin].

7. A composition of matter stabilized against deterioration which comprises a polyolefin; from about 0.005 to 5% by weight of a phenolic antioxidant; and from about 0.005 to 5% by weight of a compound according to claim 1.

8. A composition according to claim 7 wherein the polyolefin is polypropylene.

* * * * *